April 1, 1975 J. A. YOUDATH Plant Pat. 3,697
YEW TREE
Filed Jan. 10, 1974
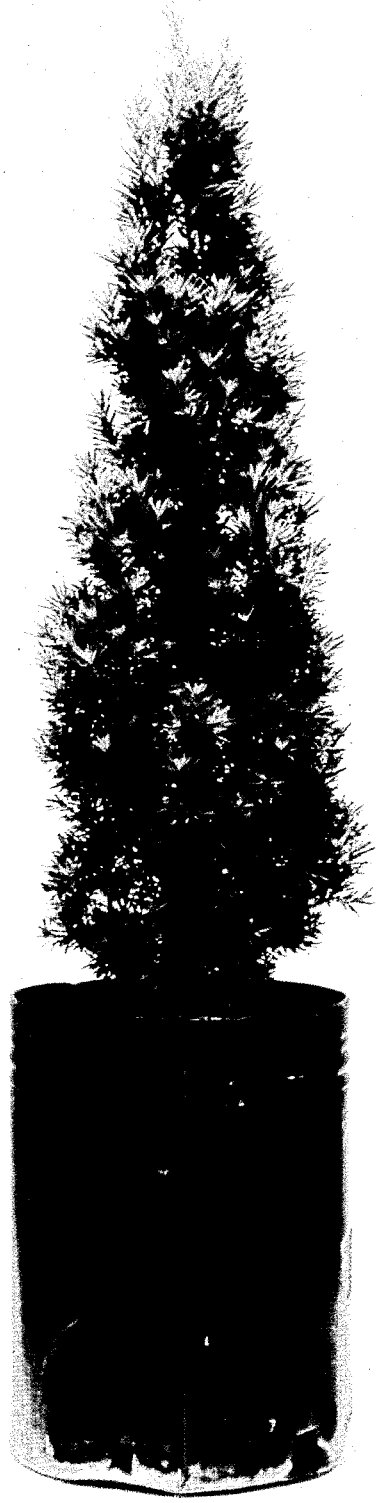

United States Patent

Plant Pat. 3,697
Patented Apr. 1, 1975

3,697
YEW TREE

John A. Youdath, 1250 E. 6th St.,
Beaumont, Calif. 92223

Filed Jan. 10, 1974, Ser. No. 432,224
Int. Cl. A01h 7/00
U.S. Cl. Plt.—50 1 Claim The present invention relates to a new and distinct variety of yew, which is characterized particularly by its vigorous, naturally dense, upright growth habit, and a conical or sometimes columnar form, producing symmetrical, almost perfect specimens with little or no pruning or shaping. The slender, upright branches and branchlets ascend almost vertically, with numerous stems densely clothed with dark green foliage. In the spring, starting about May 1st, and continuing to August, each leaf is edged with gold, and the stems have a golden cast, giving the tree a luminous golden tint.

The present variety originated from seeds collected by me from a Hicks Yew (*Taxus media hicksi*) which was growing side-by-side with a variegated English Yew (Variegated *Taxus baccata*) in my nursery at Mentor, Ohio. Two years after planting the seeds, I had about 1000 strong seedlings, and among these were three variegated plants having distinctively different gold-edged leaves, two of which plants were upright, and the third low and spreading. The upright seedlings were kept under close observation, and numerous cuttings were taken from them.

Asexual reproduction of my new variety by cuttings has been performed by me over a period of several years in Mentor, Ohio, and in Beaumont, Calif., and the distinguishing characteristics of the plant come true to form and are established and transmitted through succeeding propagations.

My new variety of yew makes a very desirable evergreen landscaping tree, as it is vigorous growing, densely clothed with dark green foliage, compact and symmetrical in form with little or no shaping or pruning, and is a male tree producing only pollen, with no berries or seeds. It is hardy down to −20° F., and is disease-resistant.

The most distinguishing characteristic of my new yew tree, however, is that in the spring, the leaves on the new growth become edged with gold, while the stems become pale yellow in color, with the result that the tree develops a beautiful golden tint. Toward the end of August, the golden edges of the leaves disappear, and the leaves become solid green. At the same time, the stems become grass green. Because of this striking characteristic of developing a touch of gold in the springtime, I have named the variety "Springold."

The accompanying drawing shows a typical tree of my new variety, showing the foliage depicted in color as nearly true as it is reasonably possible to make the same in a color illustration of this character.

The following is a detailed description of my new variety, as based on my observations of specimens grown at Beaumont, Calif., with color terminology and identifications in accordance with "A Dictionary of Color" by Maerz and Paul:

Form: Vigorous growing; upright; with naturally symmetrical conical or columnar form.

Growth habit: Branches and branchlets ascend almost vertically, with numerous stems densely clothed with leaves.

Leaves: Lanceolate, or grass-like, without resin-ducts.
- *Length*—About 1¼ to 1½ inches.
- *Width*.—About ⅛ inch.
- *Color*.—Upper surfaces dark green (Plate 23–H–8), with marginal edges of golden yellow (Plate 17–L–2) from about May 1st to about August 1st; lower surfaces grass green (Plate 21–L–5).

Stems: Grape green (Plate 21–J–1) during late summer, autumn and winter; turning to pale yellow (Plate 17–I–40) from about May 1st to August 1st.

Fruit: None.

I claim:

1. A new and distinct variety of yew tree, substantially as shown and described herein, characterized particularly by its vigorous, naturally dense upright growth habit, and conical or sometimes columnar form, producing symmetrical, almost perfect specimens with little or no pruning or shaping; the slender upright branches ascending almost vertically, with numerous stems densely clothed with dark green lanceolate leaves; the marginal edges of the leaves on new growth turning golden yellow from about May 1st to about August 1st; and the stems of the leaves also turning pale yellow at the same time.

No references cited.

ROBERT E. BAGWILL, Primary Examiner